United States Patent [19]

Harder et al.

[11] Patent Number: 5,228,447
[45] Date of Patent: Jul. 20, 1993

[54] SHOCKWAVE GENERATOR HAVING AN ULTRASOUND APPLICATOR SHIELDED FROM SHOCKWAVES

[75] Inventors: Rudolf Harder, Forchheim; Gert Hetzel, Erlangen; Hans Kaarmann, Buckenhof; Georg Koehler, Geisfeld; Hermann Kuehnke, Aurachtal-Muenchaurach; Arnim Rohwedder; Ulrich Schaetzle, both of Erlangen, all of Fed. Rep. of Germany

[73] Assignee: Siemens Aktiengesellschaft, Munich, Fed. Rep. of Germany

[21] Appl. No.: 646,838

[22] Filed: Jan. 28, 1991

[30] Foreign Application Priority Data

Feb. 12, 1990 [EP] European Pat. Off. .......... 90102737

[51] Int. Cl.⁵ .............................................. A61B 17/22
[52] U.S. Cl. .......................... 128/660.03; 128/24 EL
[58] Field of Search ......... 128/660.03, 24 EL, 660.01, 128/662.03; 606/128

[56] References Cited

U.S. PATENT DOCUMENTS 4,620,545 11/1986 Shene et al. .
4,674,505 6/1987 Pauli et al. .
4,844,081 7/1989 Northeved et al. ............ 128/24 EL
4,928,672 5/1990 Grasser et al. ......................... 128/24

FOREIGN PATENT DOCUMENTS

88G3299 2/1988 Fed. Rep. of Germany .
2587493 3/1987 France .

*Primary Examiner*—Ruth S. Smith
*Attorney, Agent, or Firm*—Hill, Van Santen, Steadman & Simpson

[57] ABSTRACT

A shockwave generator for extracorporeal lithotripsy has a housing filled with an acoustic propagation medium, through which shockwaves propagate, and in which an ultrasound applicator is disposed for locating a calculus to be treated. The ultrasound applicator has components which may be damaged if traversed by shockwaves. At least a portion of the ultrasound applicator in which these components are disposed is therefore acoustically shielded with a substance having an acoustic impedance substantially differing from the acoustic impedance of the propagation medium, so that essential parts of the shockwaves are reflected thereby and thus the non-reflected parts do not reach the shielded portion of the ultrasound applicator with sufficient energy to damage the compartments.

6 Claims, 3 Drawing Sheets

SHOCKWAVE GENERATOR HAVING AN ULTRASOUND APPLICATOR SHIELDED FROM SHOCKWAVES

BACKGROUND OF THE INVENTION

1. Field of the Invention

The present invention is directed to a shockwave generator of the type preferably suitable for use in extracorporeal lithotripsy, and in particular to such a shockwave generator having an acoustic applicator contained therein for locating a calculus to be treated and for monitoring the progress of the treatment.

2. Description of the Prior Art

A shockwave generator having an ultrasound applicator therein, which is used to locate a calculus to be treated and to monitor the progress of the treatment, is disclosed in European Application 0 301 360, corresponding to U.S. Pat. No. 4,928,672. This shockwave generator permits non-invasive disintegration of calculi in a patient, and has a housing in which a shockwave source is contained. The shockwave source introduces shockwaves into a fluid propagation medium contained within the housing, and has an application end closed with a flexible sack. The shockwaves are focussed with an acoustic lens also disposed within the housing. To align the shockwave generator relative to the body of the patient to be treated, so that the calculus to be disintegrated is situated in the focus of the shockwaves, this known shockwave generator has an ultrasound applicator, which is part of an ultrasound locating system. The ultrasound applicator generates an ultrasound image of the region of the body which surrounds the focus. The ultrasound applicator is accommodated in a central bore of the shockwave generator so as to be longitudinally displaceable. The ultrasound applicator must be pressed against the body surface of the patient with the interposition of a flexible membrane. Although a region free of shockwaves is inherently present, as a consequence of the central bore which is provided for the acceptance of the ultrasound applicator, the applicator is nonetheless traversed when pressed against the patient's body by portions of propagating shockwaves, so that there is the risk that components inside of the ultrasound applicator will be damaged. Moreover, there is the risk that the housing surrounding the ultrasound transducer will be damaged due to cavitation effects so that water can penetrate into the oil-filled interior of the ultrasound applicator housing, resulting in failure of the ultrasound applicator.

German utility model 88 09 253 discloses a similar shockwave generator. In this structure, also, an acoustic lens is provided for focussing the shockwaves generated by the shockwave source. To correct for imaging errors, a hollow, conical deflection member is arranged in the propagation path of the shockwaves. The deflection member has a surface consisting of brass or steel. Water is provided as the propagation medium for the shockwaves. An ultrasound applicator of an ultrasound locating system is disposed in the interior of the hollow, conical member. The hollow, conical member is intended to protect the ultrasound applicator against the influence of the shockwaves. Because the fundamental frequency of the shockwaves generally lies at 0.5 MHz, and a noticeable acoustic blocking effect can only be achieved when the wall thickness of the hollow, conical member is at least the same as a wavelength of the fundamental oscillation of a shockwave propagating in the material of the hollow, conical member, a wall thickness of at least 9 mm would be required, given brass as the material of the hollow, conical member. This is based on a sound propagation speed of approximately 4500 m/s in brass. Such a wall thickness of the hollow, conical member is not practical, if only for space reasons. To protect the ultrasound applicator against parts of the shockwaves which penetrate through the wall of the hollow, conical member, the interior of the hollow, conical member is filled with an expanded plastic material, which absorbs the portions of the shockwaves which penetrate through the wall. An effective protection of the ultrasound applicator is possible in this known device, therefore, only if the hollow, conical member has a sufficient wall thickness, and also if a sufficiently thick layer of expanded plastic material is present between the wall and the ultrasound applicator. This known solution also requires a substantial structural space. Moreover, specific measures for holding the hollow conical member must be provided, further increasing the structural outlay.

SUMMARY OF THE INVENTION

It is an object to provide a shockwave generator having an ultrasound applicator of an ultrasound locating system disposed therein, which is at least partially within the path of shockwaves, wherein the ultrasound applicator is shielded, at least partially, against the influence of such shockwaves as may traverse the ultrasound applicator in a simple, economic and space-saving structure.

It is a further object of the present invention to provide an ultrasound applicator which can be used in a propagation medium traversed by acoustic shockwaves without risk of damage to the ultrasound applicator.

The above objects are achieved in accordance with the principles of the present invention in shockwave generator wherein at least one part of the ultrasound applicator, which is situated in the propagation path of the shockwaves, is preceded in the direction of shockwave propagation by a substance having an acoustic impedance which deviates considerably from the acoustic impedance of the acoustic propagation medium. As used herein, an acoustic impedance which "deviates considerably" from the acoustic impedance of the acoustic propagation medium is intended to mean a deviation on the order of magnitude of at least a power of ten. As a consequence of this considerable deviation in acoustic impedance, those portions of the shockwaves which could damage the ultrasound applicator are substantially reflected at the boundary surfaces of the substance with the non-reflected part of the portions of the shockwaves which could damage the ultrasound applicator being the smaller the greater the deviation in the respective acoustic impedances of the substance and the propagation medium.

The presence of the substance can be limited in a space-saving manner to those regions of the ultrasound applicator which are situated in the propagation path of those portions of the shockwaves which could proceed to the parts of the ultrasound applicator which would be at risk to damage by such shockwaves. In this regard, it is not only the direct path from the shockwave source to the damageable parts which must be taken into account as being within the propagation path, but also damage as a result of shockwaves can occur due to diffraction or reflection of shockwaves. An effective acoustic shielding with respect to the non-reflected shockwave portions is achieved in a preferred embodiment wherein the substance is provided in the form a layer having thickness which is at least equal to a wavelength of the fundamental oscillation of the shockwave which is propagating in the substance. To achieve this result, given a low structural volume, the substance is a material wherein the sound speed is considerably lower than the speed of sound in the acoustic propagation medium. An extremely high acoustic shielding is thereby achieved with a very low layer thickness.

The substance used for acoustic shielding is preferably as gaseous medium, such as air. It has been shown that an air or gas volume having a layer thickness of few millimeters, measured in the propagation direction of the shockwaves given a liquid acoustic medium, results in a reduction in the acoustic power of the shockwaves in the region of the ultrasound transducer on an order of magnitude of a power of ten. It is thus clear that the acoustic shielding achieves protection of the ultrasound applicator against the influence of shockwaves in a simple, economic and space-saving manner.

As used herein, a "considerably lower" sound speed in the substance compared to the speed of sound in the acoustic propagation medium is a sound speed which is at most one-third of the speed of sound in the propagation medium.

To maintain the substance in place, particularly if a gaseous medium is used, the substance may be enclosed in the pores of a closed-pore expanded material, or in a conduit having a plurality of turns surrounding the ultrasound applicator, or may be enclosed in hollow members, such as beads, embedded in a carrier material. Alternatively, a chamber containing the gaseous medium may be provided which surrounds the ultrasound applicator.

For a shockwave generator having an ultrasound applicator with a housing having an acoustic exit window for the emergence of the ultrasound waves, in a further embodiment of the invention the substance precedes the housing in a region which substantially adjoins and surrounds the acoustic exit window. An effective protection of the ultrasound applicator is thereby achieved without degrading the acoustic exit. If the housing is in the form of an approximately tubular section which is terminated by the acoustic exit window, the acoustic shielding may be contained in a substantially tubular region adjoining the sound exit window, and annularly surrounding the window.

An ultrasound applicator is also disclosed herein having at least one region of its housing surrounded by a volume of a substance having an acoustic impedance which differs considerably from the acoustic impedance of body tissue. For medical applications, a substance having an acoustic impedance which matches the acoustic impedance of body tissue as exactly as possible is usually employed as the propagation medium, therefore if the acoustic impedance of the acoustic shielding substance differs substantially from that of body tissue, it will also differ substantially from the acoustic impedance of the propagation medium, thereby resulting in a reflection of shockwaves at the boundary surfaces of the substance, as described above. In a preferred embodiment of the ultrasound applicator the substance is provided in a layer thickness which is at least equal to a wavelength of the fundamental oscillation of a shockwave propagating in the substance, and it is also preferred that the speed of sound in the substance be considerably lower than the speed of sound in body tissue.

Description of the Preferred Embodiments

Figure 1:
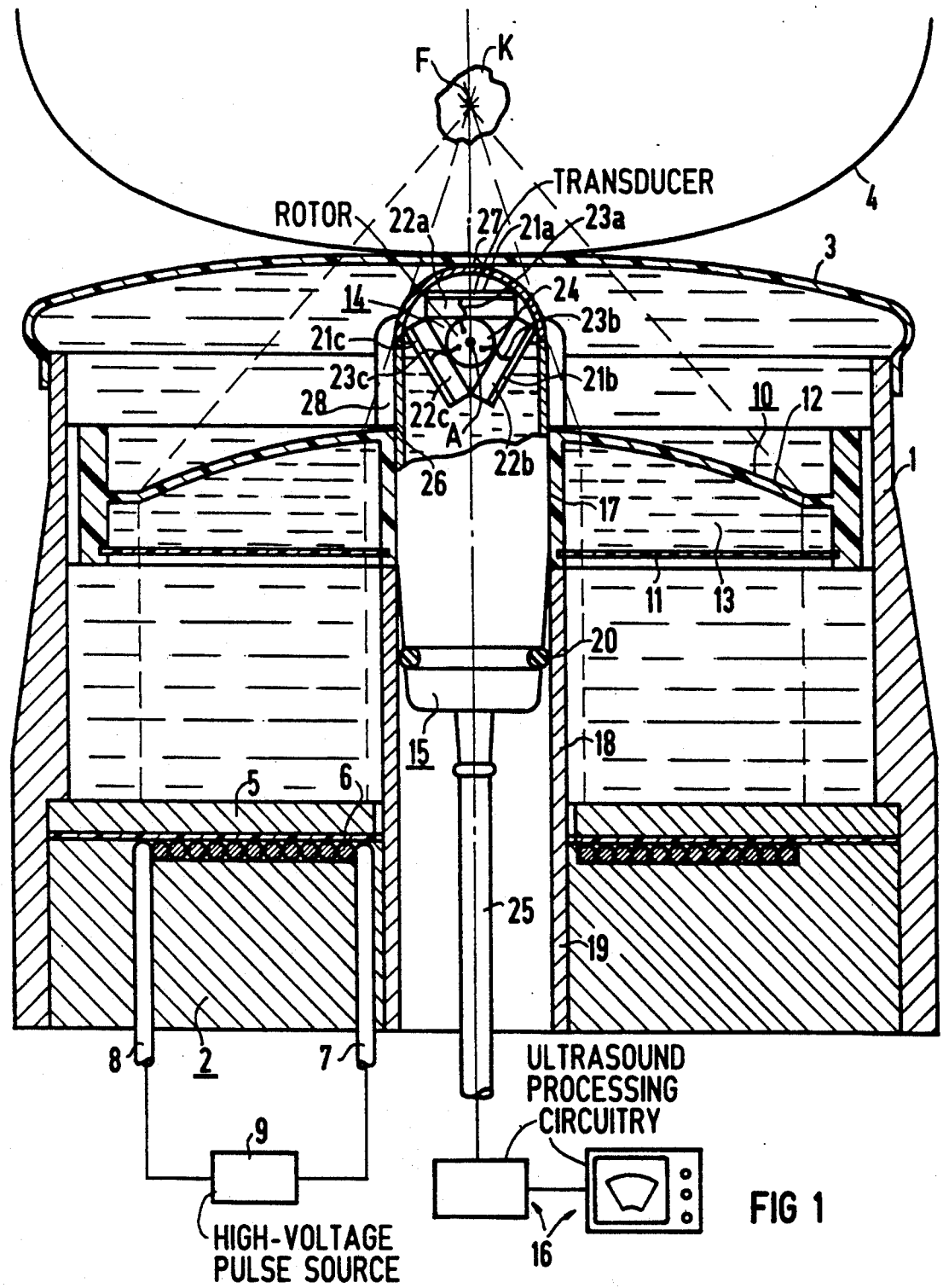
FIG. 1 is a side view in longitudinal section through a shockwave generator constructed in accordance with the principles of the present invention and having an ultrasound applicator constructed in accordance with the principles of the present invention contained therein.

A shockwave generator is shown in FIG. 1 constructed in accordance with the principles of the present invention, which is for the purpose for disintegrating a calculus K, for example a kidney stone, situated in a patient in a non-invasive manner. The shockwave generator has a substantially tubular housing 1 having a shockwave source, generally referenced 2, disposed at one end thereof. The opposite end of the housing 1 is closed with a flexible bellows 3, which permits the shockwave generator to be pressed against the body 4 (shown in cross section) of a patient to be treated, for acoustically coupling the shockwave generator to the patient. The interior of the housing 1 is filled with water which serves as an acoustic propagation medium for the shockwaves emanating from the shockwave source 2.

The shockwave source 2 is an electromagnetic shockwave source, as described in greater detail in German OS 33 28 051. The shockwave source 2 has a planar, annular membrane 5 with one side adjacent to the propagation medium situated in the housing 1. The opposite side of the membrane 5, which consists of electrically conductive material, is disposed adjacent a flat ("pancake") coil 6, having helical turns connected via terminals 7 and 8 to a pulse generator 9, with which the coil 6 can be charged with high-voltage pulses. When the coil 6 is charged with a high-voltage pulse, the membrane 5 is rapidly repelled from the coil 6. As a consequence of this motion, a substantially planar pressure pulse is introduced into the propagation medium, which is intensified to form a shockwave as it traverses through the propagation medium. For simplicity, the term "shockwave" will be used herein to refer to the shockwave in all forms, including its incipient form. The propagation direction of the shockwaves corresponds to the center axis of the shockwave source.

To focus the planar shockwaves in the manner necessary to disintegrate calculi, an acoustic collecting lens, generally referenced 10, is disposed in the propagation medium in the housing 1 between the shockwave source 2 and the bellows 3. The acoustic collecting lens 10 is a liquid lens. The lens 10 has an entry wall 11 consisting of polymethylpentene (TPX), an exit wall 12 consisting of Teflon ® (polyfluorotetraethylene), and contains a lens liquid 13, which is a fluorocarbon liquid, for example Flutech PP3 ® or Fluorinert FC 75 ®. Because the speed of sound in the lens liquid is lower than the speed of sound in water, the planoconvex shape of the collecting lens 10 causes a focussing of the initially planar shockwaves to a focal zone reference F, which lies on the center axis of the shockwave source 2.

To align the shockwave generator and the body 4 of the patient to be treated relative to each other such that the calculus K is located in the focus F, as shown in FIG. 1, an ultrasound applicator 15 is provided which is a mechanical sector scanner. The applicator 15 is part of an ultrasound imaging system which includes signal processing circuitry 16 which operates in a known manner to generate ultrasound B-images of a slice of the patient 4 containing the center axis of the shockwave source and the focus F of the shockwaves.

In the position shown in FIG. 1, the ultrasound applicator 15 is contained in a central bore 17 of the collecting lens 10, the bore 17 continuing in a tube 18 which extends through a central bore 19 of the shockwave source 2. The tube 18 is connected liquid-tight both to the collecting lens 10 and the shockwave source 2. The ultrasound applicator 15 is longitudinally displaceable in the bore 17 and in the tube 18, and is rotatable around the center axis of the shockwave source 2, with known corresponding adjustment means not being shown. A schematically indicated sealant 20 assures that the ultrasound applicator 15 will be maintained liquid-tight in the bore 17 and in the tube 18.

As can be seen from the partially broken away view of the ultrasound applicator 15, the applicator contains three ultrasound transducers, 21a, 21b and 21c, each of which is adhered to respective backings 22a, 22b and 22c. The ultrasound transducers 21a, 21b and 21c are secured to a rotor 14 at backings 22a, 22b and 22c. The rotor 14 is rotated by a motor (not shown) through a suitable drive system for rotation around an axis A, which proceeds at a right angle relative to the center axis of the shockwave source 2. The signals required for imaging are transmitted from the transducers 21a, 21b and 21c to the processing circuitry 16 and vice versa, via schematically indicated lines 23a, 23b and 23c. The transducers 21a, 21b and 21c are connected to the lines 23a, 23b and 23c, which are connected via wiper contact 24 to a cable 25 leading to the processing circuitry 16.

The ultrasound applicator 15 has a hollow, approximately cylindrical, tubular housing 26 which contains the transducers 21a, 21b and 21c. The end of the housing 26 facing the focus F is domed-shaped, and serves as a sound exit window 27 for the ultrasound waves generated by the applicator 15. The volume of the housing 26 in which the transducers 21a, 21b and 21c are contained is filled with a liquid, for example, a suitable oil.

As can be seen from the edges of the shockwaves shown in dashed lines in FIG. 1, the ultrasound applicator 15 is traversed or brushed by shockwave fronts of the region of the transducers 21a, 21b and 21c when the ultrasound applicator presses against the surface of the patient 4, with the interposition of the bellows 3, in the manner required for good image quality. Portions of the shockwaves can proceed into the liquid-filled interior of the ultrasound applicator 15. In known shockwave generators and known ultrasound applicators, there is thus the risk that components in the interior of the ultrasound applicator 15 will be damaged by the shockwaves. There is also the risk that the housing 26 will be cracked or otherwise damaged by the action of the shockwaves as a consequence of cavitation, permitting penetration of water into the interior of the ultrasound applicator 15.

To avoid these damages, which will result in failure of the ultrasound applicator or of the shockwave generator, an air volume enclosed in a chamber 28 which annularly surrounds the ultrasound applicator 15 is disposed preceding that region of the housing 26 of the ultrasound applicator 15 situated in the propagation path of the shockwaves. The chamber 28 has one end approximately adjacent the acoustic exit window 27, and extends over a length along the tubular housing 26 so that the air volume is situated in the propagation path of those parts of the shockwaves which could proceed to the ultrasound transducers 21a, 21b and 21c. The air volume does not extend in front of the region of the closure portion of the housing serving as the acoustic exit window 27, because this would degrade propagation of the ultrasound waves generated by the ultrasound applicator 15. The chamber 28 is in gap-free contact with the surface of the housing 26, and is glued thereto. The chamber 28 has dimensions, measured in the propagation direction of the portions of the shockwaves, so that the enclosed air volume has a layer thickness which is at least equal to a wavelength of a shockwave generated by the shockwave source 2 and propagating in the air volume. Since air is a substance having an acoustic impedance which differs considerably from the acoustic impedance of the water, which is used as the acoustic propagation medium for the shockwaves (the acoustic impedance of water is approximately the same as the acoustic impedance of body tissue, while the acoustic impedance of air is several powers of ten less than that of water), a substantially complete reflection of the portions of the shockwaves incident on the air volume occurs at the boundary surfaces of the air volume. The air volume, whose layer thickness traversely relative to the center axis of the shockwave generator 2 is a few millimeters, thus represents an effective acoustic shielding for the non-reflected portions of the shockwave. This is because, given an assumed frequency of 0.5 MHz for the fundamental oscillation of the shockwaves generated by the shockwave source 2, the wavelength of the fundamental oscillation is less than 1 mm, given a speed of sound of 340 m/s.

Figure 2:
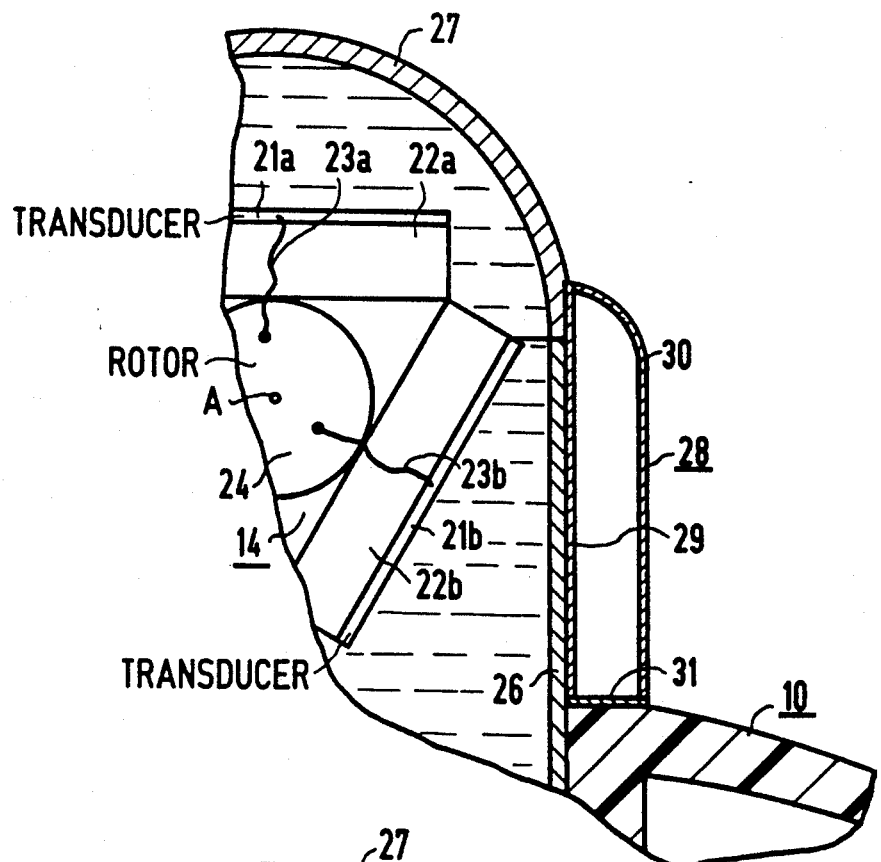
FIG. 2 is an enlarged view of a longitudinal section through a detail of the ultrasound applicator of FIG. 1.

In the embodiment of FIG. 1, the air volume is enclosed within the chamber 28, which may be formed of sheet brass, as shown in greater detail in FIG. 2. The chamber 28 has a cylindrical, tubular inside wall 29, which is surrounded by an outside wall 30 which tapers at one end. The inside wall 29 has one end joined, for example by soldering, to the corresponding end of the outside wall 30. At their opposite ends, the inside wall 29 and the outside wall 30 are joined, for example by soldering as well, to an annular base 31, so that the inside wall 29, the outside wall 30 and the base 31 of the chamber 28 hermetically enclose the air volume contained therein.

Figure 3:
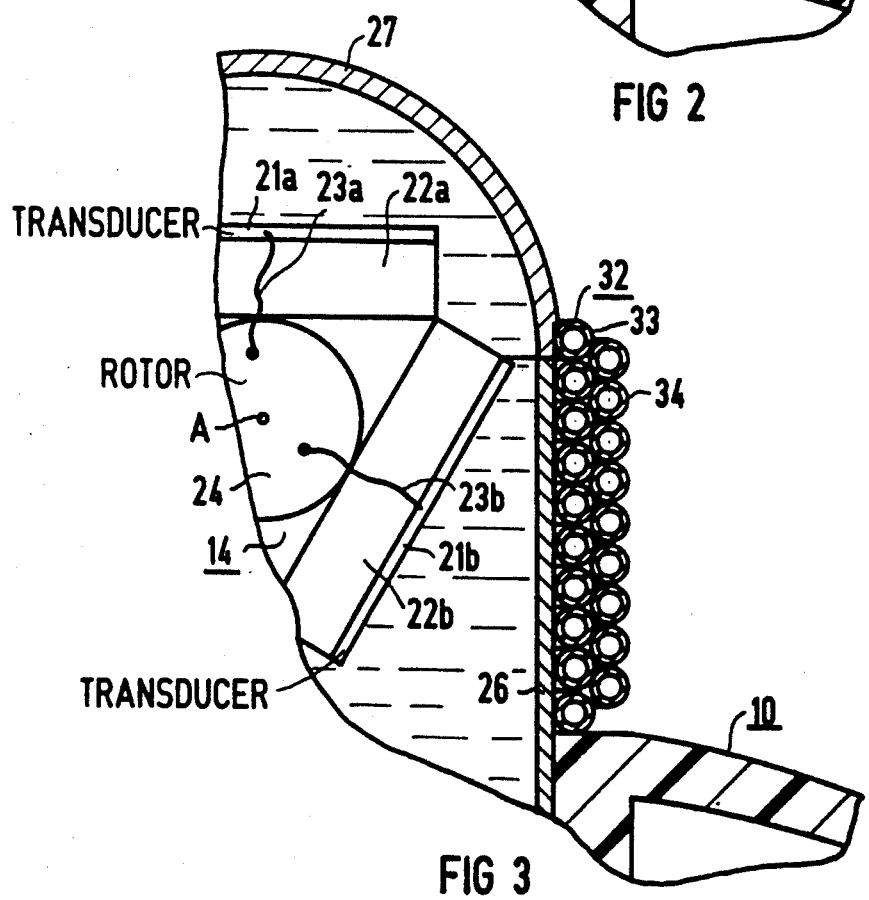
FIGS. 3, 4 and 5 respectively show further embodiments of the enlarged detail of FIG. 2.

In the embodiment of FIG. 3, the air volume is enclosed in a plastic conduit 32 which is tightly closed at each of its ends. The plastic conduit 32 is wound in a first layer 33 around the housing 26 in a pluralliy of turns, and is attached to the housing 26 by suitable adhesive. The plastic conduit 32 continues in a second layer 34 which is wound over the first layer 33, and is also joined thereto by adhesive. Particularly given the use of a degasified liquid as the propagation medium, air may slowly diffuse through the plastic material of the conduit 32 into the liquid, therefore the conduit 32 should have a sufficiently rigid wall in order to prevent it from being pressed flat under the static pressure of the liquid, which would mean that the air volume enclosed within the conduit 32 would no longer be present in the intended layer thickness.

Figure 4:
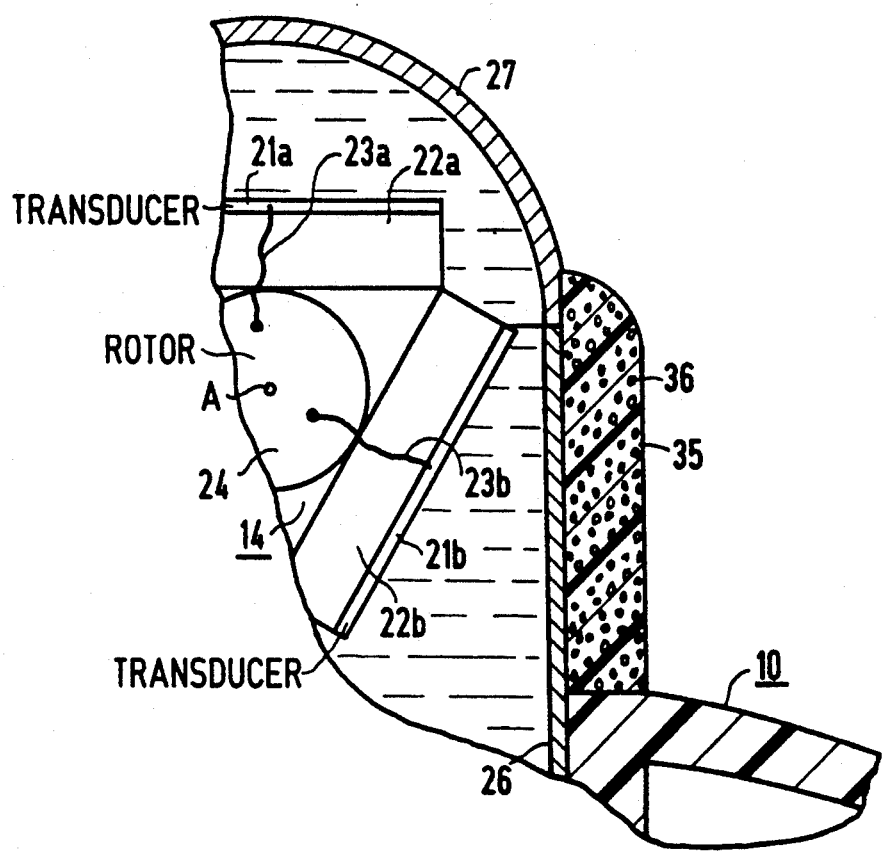

As shown in FIG. 4, the air volume may alternatively be enclosed in the pores 36 of a closed-pore member 35 formed of plastic foam. The member 35 may be formed, for example, from expanded polyurethane. The member 35 is glued to the housing 26 with a suitable adhesive.

Figure 5:
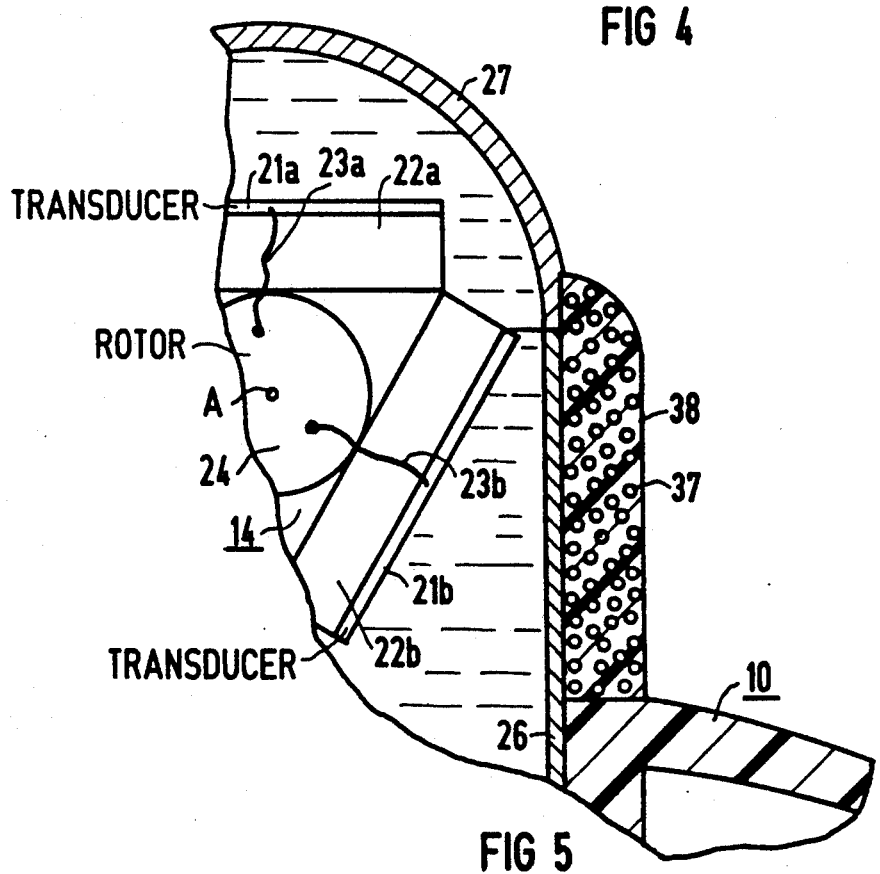

A further embodiment is shown in FIG. 5 wherein the air volume is contained in a plurality of extremely small hollow elements or beads 37. The size of the beads 37, as the size of the pores 36 in the embodiment of FIG. 4 is shown enlarged in exaggerated fashion. The hollow members 37 are embedded in a casting compound 38. Small, hollow glass or plastic beads can be employed as the hollow members 37. For example, silicone rubber may be used as the casting compound 38, which simultaneously serves the purpose of fixing the hollow members 37 relative to the housing 26.

Instead of being preceded by air, the ultrasound applicator 15, i.e., the housing 26 thereof, can be preceded by a different gaseous, liquid or solid substance, as long as the substance has an acoustic impedance differing substantially from the acoustic impedance of the acoustic propagation medium, which need not necessarily be water. For the reasons already described, substances wherein the speed of sound is low with respect to the speed of sound in the acoustic propagation medium are preferable, because the layer thickness of the substance required for acoustic shielding can therefore be maintained small.

The shielding in the form of the chamber 28, the conduit 32, the pores 35 or the hollow members 37 may be connected to the shockwave generator or to the ultrasound applicator 15, as shown in the exemplary embodiments.

The collecting lens is shown as a liquid lens for exemplary purposes only, and it will be understood by those skilled in the art that a solid collecting lens may be used as well.

Also in the exemplary embodiments, the ultrasound applicator 15 is shown as a mechanical sector scanner having a plurality of ultrasound transducers 21a, 21b and 21c attached to a rotor 14. A mechanical sector scanner having only one ultrasound transducer, which executes an oscillating motion, may be used instead. It is also possible to use an ultrasound applicator having a stationary ultrasound transducer. If the ultrasound transducer is operated as a phased array or a linear array, there is the possibility of implementing the scan in an electronic manner.

The ultrasound applicator may be integrated in the shockwave generator so that the ultrasound applicator itself does not require a separate housing. In such a case, the housing which surrounds the components of the ultrasound applicator may be a part of the shockwave generator, if such a housing is provided at all. Those components which serve the purpose of holding the acoustic shielding substance must then also be parts of the shockwave generator.

Although further modifications and changes may be suggested by those skilled in the art, it is the intention of the inventors to embody within the patent warranted hereon all changes and modifications as reasonably and properly come within the scope of their contribution to the art.

We claim as our invention:

1. In a shockwave generator for generating shockwaves having a shockwave generator housing containing a shockwave source having a central axis an acoustic propagation medium for the shockwaves, an ultrasound applicator for use in locating an object to be irradiated with said shockwaves, said ultrasound applicator being disposed in said shockwave generator housing and having an ultrasound applicator housing, the improvement comprising:

a non-acoustically reflecting member having at least one region in the shape of a hollow cylinder which surrounds said ultrasound applicator housing, and which surrounds said control axis, said member containing a material in said region having a sound propagation speed therein which is considerably lower than the sound propagation speed in said acoustic propagation medium.

2. The improvement of claim 1 wherein said member contains said material in a layer having a thickness which is at least equal to a wavelength of the fundamental oscillation of one of said shockwaves when propagating in said material.

3. The improvement of claim 1 wherein at least said region of said member is formed by a closed-pore foam, and wherein said material is enclosed in pores of said closed-pore foam.

4. The improvement of claim 1 wherein at least said region of said member is formed by a conduit containing said material, said conduit surrounding said ultrasound applicator housing in a plurality of turns.

5. The improvement of claim 1 wherein at least said region of said member is formed by a carrier substance, said carrier substance having a plurality of hollow members embedded therein, and said material being enclosed in said hollow members.

6. The improvement of claim 1 wherein said member has a cavity therein, and wherein said material is enclosed in said cavity.

* * * * *